(12) United States Patent
Zhou

(10) Patent No.: US 6,319,523 B1
(45) Date of Patent: Nov. 20, 2001

(54) COMPOSITION AND METHOD FOR INHIBITING ORAL BACTERIA

(76) Inventor: James H. Zhou, 32 Hallmark Dr., Wallingford, CT (US) 06492

( * ) Notice: Subject to any disclaimer, the term of this patent is extended or adjusted under 35 U.S.C. 154(b) by 0 days.

(21) Appl. No.: 09/606,294

(22) Filed: Jun. 29, 2000

(51) Int. Cl.[7] .......................... A61K 35/78; A01N 65/00
(52) U.S. Cl. .......................... 424/725; 424/729; 424/735; 424/752; 424/757; 424/766; 424/776; 424/777
(58) Field of Search .................. 424/195.1, 725, 424/729, 735, 752, 757, 706, 776, 777

(56) References Cited

U.S. PATENT DOCUMENTS 6,103,240 * 8/2000 Zhou ................................ 424/195.1
6,124,442 * 9/2000 Zhou et al. ........................... 536/4.1

FOREIGN PATENT DOCUMENTS

1148 * 12/1995 (WO).
684772 * 12/1995 (EP).

\* cited by examiner

Primary Examiner—Herbert J. Lilling
(74) Attorney, Agent, or Firm—Bachman & LaPointe, P.C.

(57) ABSTRACT

A composition for inhibiting oral bacteria, including a polyphenol derivative composition; and at least one composition selected from the group consisting of mogroside derivative composition, licorice extract and combinations thereof, wherein the composition is effective to inhibit growth of oral microbials.

15 Claims, No Drawings

COMPOSITION AND METHOD FOR INHIBITING ORAL BACTERIA

BACKGROUND OF THE INVENTION

The invention relates to a composition and method for inhibiting oral bacteria which are known causes of oral malodor, gum disease and tooth decay.

Many oral and dental hygiene products are available on the market and contain chemicals, chlorite, alcohol and the like which are typically characterized by bad taste and which may be toxic or at least be perceived by consumers as being toxic such that the consumer finds the product unpleasant and may be concerned as to accidental swallowing and the like.

It has recently been found that typical oral pathogens which are causative of oral malodor and other undesirable conditions including gum diseases and tooth decay develop resistance to conventional products containing such chemicals and eventually have reduced effectiveness over time.

It is clear that the need remains for a composition providing long-term and effective inhibition of oral bacteria, which is perceived by the consumer as being non-toxic and, preferably, which has a pleasant taste.

It is therefore the primary object of the present invention to provide a composition for inhibiting oral bacteria which is long-term effective.

It is a further object of the present invention to provide such a composition which is pleasant tasting.

It is a still further object of the present invention to provide such a composition which is perceived by consumers to be natural and non-toxic.

It is another object of the present invention to provide a method for inhibiting oral bacteria.

Other objects and advantages of the present invention will appear hereinbelow.

SUMMARY OF THE INVENTION

In accordance with the present invention, the foregoing objects and advantages have been readily attained.

According to the invention, a composition is provided for inhibiting oral bacteria, which composition comprises a polyphenol derivative composition; and at least one composition selected from the group consisting of mogroside derivative composition, licorice extract and combinations thereof, wherein the composition is effective to inhibit growth of oral microbials.

The composition preferably comprises polyphenol derivative composition, mogroside derivative composition and licorice extract.

In accordance with the present invention, it has been found that polyphenol derivative, mogroside derivative and licorice extract each have a weak anti-microbial effect which is enhanced and increased when any two or all three of these components are combined. Further, the polyphenol derivative composition has to be found to suppress or prevent microbial change or genetic alteration of microbials so as to suppress and/or prevent the microbial from developing resistance to the composition of the present invention.

DETAILED DESCRIPTION

The invention relates to a composition for inhibiting oral bacteria and, more particularly, to an herbal composition and method for using same which has been found effective in treating oral malodor and gum diseases, and which helps prevent tooth decay and stomach acid reflux. The composition is also effective in suppressing genetic mutation believed to be responsible for oral pathogens developing resistance to a particular agent over time.

The composition of the present invention has been found effective in inhibiting oral bacteria such as Fusob nucleatum, Strep pathogens Porph gingivalis and the like which cause oral malodor, gum disease, tooth decay and/or digestive problems.

In accordance with the present invention, a composition is provided which preferably includes a polyphenol derivative composition and at least one composition selected from the group consisting of mogroside derivative composition and licorice extract. More preferably, the composition of the present invention includes polyphenol derivative composition, mogroside derivative composition and licorice extract.

Each component of the composition of the present invention has been found to provide a particular effect, and the combination provides a synergistic effect, which inhibit undesirable microbials encountered in oral environments, and which further suppress the tendency of such microbials to alter and develop resistance to a particular suppressing or inhibiting agent. As used herein, inhibit is intended to include reduction, suppression and/or partial or total elimination of one or more undesirable microbials.

The polyphenol derivative composition component of the present invention is preferably a catechin derivative. Suitable catechin derivative can be obtained from a number of botanical sources including Camellia spp., Acacia catecha, Polygonum spp., Areca catechu, Potentilla fragarioides, Rheum, Prunus, Ginkgo biloba, Machilus, Elaeagnus, Apocynum, Geranium, and combinations thereof.

The polyphenolic fraction of tea has been called tea tannin because of the pungent taste it has on the palate. Tea polyphenols constitute most of the soluble components of tea, ranging from 15–30% of dried tea. Therefore drinking tea is in a way very much synonymous with drinking tea polyphenols. In fresh tea leaves, polyphenols exist as catechins and they remain unchanged in the manufacturing of green tea. In the case of black tea, catechins are oxidized into theaflavins or thearubigins in the course of the so-called fermentation process. They are mostly the dimers of catechins. "Crude catechins" or "crude theaflavins" have been fractionated and individual catechins and theaflavins have been further purified. With these samples, many of the physiological properties of tea polyphenols have been studied.

Catechin compositions in green tea are shown in Table 1 below:

TABLE 1

| Composition of "crude catechins" in green tea | | |
|---|---|---|
| Catechins | Absolute % | Relative % |
| (+)-Gallocatechin (GC) | 1.44 | 1.6 |
| (−)-Epigallocatechin (EGC) | 17.57 | 19.3 |
| (−)-Epicatechin (EC) | 5.81 | 6.4 |
| (−)-Epigallocatechin gallate (EGCg) | 53.90 | 59.1 |
| (−)-Epicatechin gallate (ECg) | 12.51/91.23 | 13.7/100 |

These are examples of some suitable catechins in accordance with the invention.

The polyphenol derivative preferably also includes a resveratrol derivative which can preferably be obtained from polygonum spp, grape vine, fruit, seed and skin; peanut sources; pine sources and combinations thereof. The composition preferably includes effective amounts of resveratrol selected for a particular use, and may be standardized so as to be present in an amount by weight of polyphenol derivative composition of about 3%.

The polyphenol derivative composition is preferably provided standardized to at least about 2% weight of specific polyphenol compounds as measured with respect to the entire polyphenol derivative composition, more preferably at least about 10% weight and ideally standardized to contain about 80% weight of specific polyphenol compounds.

It is particularly preferred according to the invention to provide, standardized polyphenol derivative composition which is standardized to contain at least about 25% weight, more preferably 60% weight of catechins.

The polyphenol derivative composition is known to have a weak effect on inhibiting certain microbials, and has an extremely bitter taste. In addition, the polyphenol derivative composition has been found in accordance with the present invention to substantially prevent or suppress microbial change or genetic alteration which is believed to be the vehicle whereby oral pathogens develop resistance to a particular agent over time. The polyphenol derivative composition contains or is an anti-oxidant which is known to suppress free radicals that are frequently causative of genetic alteration.

The mogroside derivative composition of the present invention is preferably a mogroside derivative or mogroside composition extracted from *Momordica grosvenorii*. Mogroside may be extracted and purified from *Momordica grosvenorii* (Cucurbitaceae subfamily), particularly from Lou Han fruit of this family, to advantageously contain at least about 4% weight of mogroside in the mogroside derivative composition. The composition may be provided having more mogroside, and it is most preferred to standardize the composition to contain about 80% weight of mogrosides.

Further, preferred mogroside is mogroside V, and the mogroside derivative composition is preferably standardized to contain at least about 2% weight of mogroside V, more preferably at least about 30% weight of mogroside V, based on total weight of the mogroside derivative composition. The balance of the mogroside derivative composition typically consists of other unspecified fruit or plant material remaining in the extract. Mogroside has been found to enhance the microbial activity of the polyphenol derivative and, further, to overcome the bitter taste of the polyphenol derivative thereby providing the composition with a more pleasant taste. In addition, mogroside has been found to possess a certain amount of microbial inhibiting activity itself.

The licorice extract is preferably the alcohol soluble and water insoluble extract of licorice, for example the extract of licorice root. Preferred licorice root is taken from *Glycyrrhiza uralensis* and related spp. including *G. glabra, G. kansuesis, G. inflata*, and the like.

Suitable alcohol for conducting the extraction is methanol, or ethanol, or both, although other alcohol may be suitable, and ethanol extraction is preferred.

The licorice extract has been found to provide a powerful inhibition of oral pathogens and microbials, particularly those responsible for oral malodor, gingivitis and other tooth decay problems.

The composition of the present invention preferably includes the polyphenol derivative composition, mogroside derivative composition and licorice extract in particular amounts. For use as an oral composition for inhibiting microbials, the composition preferably contains at least about 0.5 mg and preferably between about 0.5 and about 10 mg of the polyphenol derivative composition, as well as at least about 0.01 mg and preferably between about 0.01 and about 1 mg of mogroside derivative composition and at least about 0.01 mg and preferably between about 0.01 and about 5 mg of licorice extract. These values are given on a basis of weight per unit of composition. Thus, if a unit dose is determined to be one milliliter of a liquid suspension, the licorice suspension would contain the given amounts in milligrams of the particular composition component per milliliter.

On a weight percent basis, the composition is preferably provided containing at least about 0.05% w/v of the polyphenol derivative composition, at least about 0.01% w/v of the mogroside derivative composition and at least bout 0.001% w/v of the licorice extract.

To summarize, dosage per serving of the composition of the present invention is preferred as follows:
 Polyphenol derivatives: 0.5–20 mg/ml (0.05–2% w/v)
 Mogroside derivatives: 0.1–1 mg/ml (0.01%–0.1% w/v)
 Licorice extract: 0.01–5 mg/ml (0.001–0.5 w/v)

It should be noted that other flavors can of course be included in the composition of the present invention to provide other tastes, functions and the like. For example, additional flavoring agents can be included such as mint, fruit flavors, lemon and the like. In addition, sweetening agents can be included such as additional terpene glycoside compositions non-nutritive sweeteners and the like.

The composition may be provided as a liquid solution such as tea or other beverage or oral rinse. The composition may alternately be provided as drop or gumdrops, chewing gum, breathe dots, toothpaste and the like. Still further, the composition may advantageously be provided in granular or dry form, if desired.

The above sets forth the preferred amounts of each composition component per dose. It should of course be appreciated that in liquid or dry strength, the composition may be provided in various strengths eventually to be diluted before use. For example, the composition may be provided having a 10× strength in solution form, in which case the 10× solution would preferably have a composition as follows:
 Polyphenol derivatives: 10–100 mg/ml (1%–10% w/v)
 Mogroside derivatives: 0.1–10 mg/ml (0.01%–1% w/v)
 Licorice extract: 0.1–50 mg/ml (0.01–5 w/v)

In accordance with the present invention, each of the components of the present composition have been found to possess some amount of microbial inhibitory affect on its own, and this affect is dramatically increases when the ingredients are combined. Further, the polyphenol portion of the composition of the present invention has a strong suppressing affect on microbial change or genetic alteration, thereby helping to prevent microbial from developing resistance to the composition of the present invention over the long term. Further, the mogroside portion of the present invention serves to provide the composition with a more pleasant taste than would normally be obtained, and the licorice extract provides the strongest portion of microbial inhibition. The following examples are provided so as to further demonstrate the advantages of the composition and method of the present invention.

EXAMPLE 1

In this example, a composition was prepared including 0.1% (w/v) concentration of polyphenol derivative and 0.1%

(w/v) concentration of mogroside. This composition was tested for inhibition of fusob nucleatum (atcc 01953), which is a known oral malodor causing bacteria. Each of these ingredients was also tested separately for inhibition of fusob nucleatum. Table 2 below sets forth the minimum inhibition concentration (MIC) for each of these ingredients alone and for a combination of the ingredients.

TABLE 2

|  | Fusob nucleatum (ATCC 10953) | |
| --- | --- | --- |
| Inhibitor name | Alone | Combination |
| Polyphenol | >10 mg/ml | 0.07 mg/ml |
| Mogroside | 0.25 mg/ml | 0.06 mg/ml |

As illustrated in Table 2, a clear synergistic result is accomplished by combination of polyphenol and mogroside. While greater than 10 mg per ml was required with polyphenol alone, and 0.25 mg per ml was required with mogroside alone, a combination containing 0.07 mg/ml a polyphenol and 0.06 mg/ml of mogroside was effective at inhibiting fusob nucleatum. This advantageously allows for the composition of the present invention to prepared having effective levels of ingredients without requiring excessive amounts of same.

EXAMPLE 2

In this example, a composition was provided which included 0.1% w/v concentration of polyphenol and 0.1% w/v concentration of licorice extract (ethanol soluble and water insoluble). The composition was tested for inhibition of fusob nucleatum as described above, as were each of these ingredients separately. Table 3 below sets forth the minimum inhibition concentrations for these compositions.

TABLE 3

|  | Fusob nucleatum (ATCC 10953) | |
| --- | --- | --- |
| Inhibitor name | Alone | Combination |
| Polyphenol | >10 mg/ml | 0.07 mg/ml |
| Licorice Extract | 0.31 mg/ml | 0.08 mg/ml |

This data also clearly indicates a synergistic effect from the combination of polyphenol and licorice extract in dramatically reducing the amount of each ingredient necessary in the composition to obtain inhibition.

EXAMPLE 3

In this example, a number of different compositions each at a concentration of 0.1% w/v was tested for inhibition of the oral pathogens Strep mutans and Porph gingivalis. Table 4 below sets forth the minimum inhibition concentration in mg/ml for each of these ingredients separately.

TABLE 4

|  | Oral Pathogens | |
| --- | --- | --- |
| Inhibitor | S. mutans | Porph gingivalis |
| Ethanol extracted licorice | 0.062 mg/ml | 0.031 mg/ml |
| Water extracted licorice | No inhibition | No inhibition |

TABLE 4-continued

|  | Oral Pathogens | |
| --- | --- | --- |
| Inhibitor | S. mutans | Porph gingivalis |
| 18B-Glycyrrhetinic acid | 0.25 mg/ml | 0.137 mg/ml |
| Glycyrrhizic acid | 0.25 mg/ml | 0.125 mg/ml |
| mogroside | 0.7 mg/ml | 0.7 mg/ml |

This data shows that the licorice extract which is effective as a Porph microbial inhibitor of the composition of the present invention is the ethanol extracted portion, and further demonstrates that the water extracted portion of licorice does not have any inhibitory effect. Further, the data in Table 4 further establishes that the Porph inhibitor of the licorice extract is not glycyrrhirizic acid or 18B-glycyrrhetinic acid. The data in Table 4 also demonstrates that mogroside does have some level of microbial inhibitory effect, although not high enough for effective use alone.

EXAMPLE 4

A 10× water solution was formulated containing 100 mg/ml of polyphenol derivatives, 20 mg/ml of mogroside derivative and 10 mg/ml of licorice extract. The composition also contained 3% lemon flavor (w/v).

One milliliter of the solution was mixed with 2 teaspoons (approximately 10 ml) of water, and was given to 5 testers each of whom suffered from sore gums and sensitive teeth. The solution was taken in the mouth, used as a rinse for approximately 5 minutes, and then either swallowed or spit out. All testers reported immediate relief of the experienced symptoms and complete healing after 3 days of using the composition 3 times per day.

EXAMPLE 5

The same solution from Example 4 was used for this example, where 1 ml was mixed in one cup (approximately 6 oz) of water. The composition was given to 5 testers each of whom suffered from chronic oral malodor. Each tester held and rinsed the solution orally for approximately 3 minutes, before swallowing. Each tester experienced immediate reduction of oral malodor and malodor was completely controlled by continuous use of the composition 3 times per day.

EXAMPLE 6

The solution of Example 4 was used for this example as well, and 1 ml was mixed in a cup (approximately 6 oz) and used by 3 testers, 3 times per day. These testers suffered from oral malodor due to stomach acid reflux. The solution was used as described above, rinsing for a short period of time before swallowing. Each tester experienced an immediately reduction.of oral malodor and stomach acid, and malodor and reflux were both completely controlled through continuous use of the composition 3 times per day.

In accordance with the foregoing, it should readily be appreciated that the composition of the present invention is useful as a composition for inhibiting oral and/or digestive microbials, and particularly for use in long-term control of oral and digestive microbials. A particular advantage of the present invention is that such inhibition is obtained and the tendency of the oral microbial to genetically alter and develop resistance is at least suppressed if not completely inhibited.

This invention may be embodied in other forms or carried out in other ways without departing from the spirit or essential characteristics thereof. The present embodiment is therefore to be considered as in all respects illustrative and not restrictive, the scope of the invention being indicated by the appended claims, and all changes which come within the meaning and range of equivalency are intended to be embraced therein.

What is claimed is:

1. A composition for inhibiting oral bacteria, comprising:
   a polyphenol composition containing at least one polyphenol selected from the group consisting of Catechin, resveratrol and combinations thereof;
   a mogroside composition standardized to contain at least about 2% weight of mogroside V; and
   a licorice extract, said licorice being an organic solvent soluble and water insoluble fraction;
   wherein said composition contains at least about 0.05% w/v of said polyphenol composition, at least about 0.01% w/v of said mogroside composition and at least about 0.001% w/v of said licorice extract.

2. A method for inhibiting oral bacteria, comprising the steps of:
   providing a composition according to claim 1; and
   orally administering said composition to a mammal, whereby oral microbials are inhibited and suppressed from genetically altering.

3. The composition according to claim 1, wherein said composition contains said polyphenol composition, said mogroside composition and said licorice extract in amounts per unit composition as follows:
   polyphenol composition 0.5–10 mg
   mogroside composition 0.1–1 mg
   licorice extract 0.01–5 mg.

4. The composition according to claim 1, wherein said polyphenol composition comprises Catechin.

5. The composition according to claim 4, wherein said Catechin is obtained from at least one botanical source selected from the group consisting of Camellia spp., *Acacia catechu*, Polygonum spp., Areca catechu, *Potentilla fragarioides*, Rheum, Prunus, *Ginkgo biloba*, Machilus, Elaeagnus, Apocynum, Geranium, and combinations thereof.

6. The composition according to claim 4, wherein said polyphenol composition further comprises resveratrol.

7. The composition according to claim 6, wherein said resveratrol is obtained from at least one source selected from the group consisting of polygonum spp., grape vine, fruit, seed and skin; peanut; pine and combinations thereof.

8. The composition according to claim 1, wherein said polyphenol composition is standardized to contain at least about 2% wt polyphenol compounds.

9. The composition according to claim 1, wherein said polyphenol composition is standardized to contain at least about 80% wt polyphenol compounds.

10. The composition according to claim 1, wherein said mogroside composition comprises an extract of *Momordica grosvenorii*.

11. The composition according to claim 1, wherein said mogroside composition is standardized to contain at least about 40% wt of mogroside compounds.

12. The composition according to claim 1, wherein said mogroside composition is standardized to contain at least about 80% weight of mogroside compounds.

13. The composition according to claim 1, wherein said mogroside composition is standardized to contain at least about 30% weight of mogroside V.

14. The composition according to claim 1, wherein said licorice extract comprises licorice root extract.

15. The composition according to claim 1, wherein said licorice extract comprises extract obtained from a source selected from the group consisting of *Glycyrrhiza uralensis, G. glabra, G. kansuesis, G. inflata* and combinations thereof.

* * * * *